US012576238B2

(12) United States Patent
White et al.

(10) Patent No.: US 12,576,238 B2
(45) Date of Patent: Mar. 17, 2026

(54) CATHETER AND TUBE ASSEMBLY AND METHOD OF USE

(71) Applicant: PATIENT SHIELD CONCEPTS, LLC, Denver, CO (US)

(72) Inventors: Lynn Rosen White, Denver, CO (US); Debora I-Ping Ma, Lafayette, CO (US)

(73) Assignee: PATIENT SHIELD CONCEPTS, LLC, Denver, CO (US)

( * ) Notice: Subject to any disclaimer, the term of this patent is extended or adjusted under 35 U.S.C. 154(b) by 1087 days.

(21) Appl. No.: 17/296,523

(22) PCT Filed: Nov. 25, 2019

(86) PCT No.: PCT/US2019/063108
§ 371 (c)(1),
(2) Date: May 24, 2021

(87) PCT Pub. No.: WO2020/107035
PCT Pub. Date: May 28, 2020

(65) Prior Publication Data
US 2022/0126059 A1     Apr. 28, 2022

Related U.S. Application Data

(60) Provisional application No. 62/771,154, filed on Nov. 25, 2018, provisional application No. 62/771,162, filed on Nov. 25, 2018.

(51) Int. Cl.
*A61M 25/00*     (2006.01)
*A61M 27/00*     (2006.01)

(52) U.S. Cl.
CPC .... *A61M 25/0017* (2013.01); *A61M 25/0015* (2013.01); *A61M 25/003* (2013.01);
(Continued)

(58) Field of Classification Search
CPC ...... A61M 25/0015; A61M 2025/0036; A61M 2025/004
See application file for complete search history.

(56) References Cited

U.S. PATENT DOCUMENTS

| | | | |
|---|---|---|---|
| 5,695,457 A | * | 12/1997 | St. Goar ............ A61M 1/3659 |
| | | | 604/509 |
| 5,772,639 A | | 6/1998 | Lampropoulos et al. |
| 2005/0283111 A1 | | 12/2005 | Maurice |

FOREIGN PATENT DOCUMENTS

| | | |
|---|---|---|
| CN | 202336141 U | 7/2012 |
| JP | 2001513357 A | 9/2001 |

(Continued)

OTHER PUBLICATIONS

International Search Report and Written Opinion mailed Apr. 20, 2020 for International Application No. PCT/US2019/063108, filed Nov. 25, 2019.

*Primary Examiner* — Dung T Ulsh
(74) *Attorney, Agent, or Firm* — Ashfields Law P.C.; Nell G. J. Mothew

(57) ABSTRACT

A device has a drainage conduit for draining fluids from a patient. The drainage conduit may be flexible. One or more flexible delivery conduits deliver medication to the patient. The one or more flexible delivery conduits are attached to the flexible drainage conduit. The one or more flexible delivery conduits are detachable from the flexible drainage conduits at at-least one end of the drainage conduit so that the delivery conduits can be peeled off the drainage conduit at the proximal and deployed with the proximal ends of the delivery conduits separated from the proximal end of the drainage conduit.

11 Claims, 10 Drawing Sheets

(52) U.S. Cl.
CPC ..... *A61M 27/00* (2013.01); *A61M 2025/0019*
(2013.01); *A61M 2025/0031* (2013.01); *A61M*
*2025/0036* (2013.01); *A61M 2025/004*
(2013.01)

(56) References Cited

FOREIGN PATENT DOCUMENTS

| JP | 2015180275 | A | 10/2015 |
|----|----|----|----|
| WO | 2005120621 | A1 | 12/2005 |
| WO | WO 2005/120621 | | 12/2005 |
| WO | 2006002103 | A2 | 1/2006 |
| WO | WO 2006/002103 | | 1/2006 |

* cited by examiner

Delivery Conduits 308

Drainage Conduit 702

Proximal End 104

Drainage Device 100

Distal End 102

Drainage Conduit 302

Delivery Conduits 308

Delivery Conduits 308

Detail 700

Delivery Conduits 308a and b

Delivery Conduits 308c and d 312a-d

Drainage Conduit 302

DETAIL J
SCALE 4 : 1

FIG. 10B
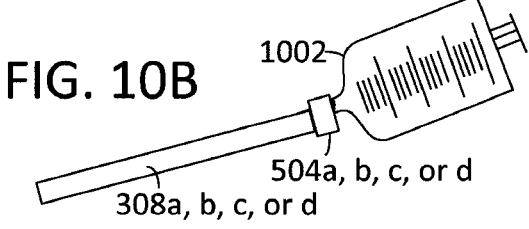
1002
504a, b, c, or d
308a, b, c, or d
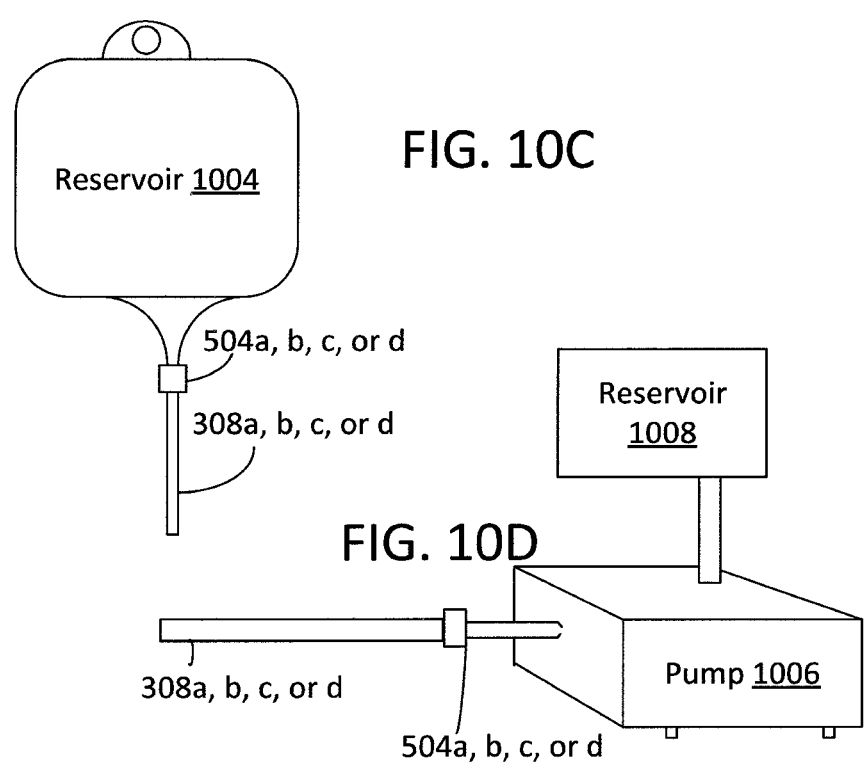
FIG. 10C
Reservoir 1004
504a, b, c, or d
308a, b, c, or d
FIG. 10D
Reservoir 1008
Pump 1006
308a, b, c, or d
504a, b, c, or d

302

302

1200

Start

Form Drainage Conduit 1202

Form Delivery Conduit 1204

Form Luer Locks 1206

Attach Form Luer Locks 1208

Insert Delivery Conduit Into Channels 1210

Optionally Bond a portion of Each Deliver Conduit to Channel 1212

End

CATHETER AND TUBE ASSEMBLY AND METHOD OF USE

CROSS-REFERENCE TO RELATED APPLICATIONS

The present application is a U.S. national phase of PCT International Patent Application No. PCT/US2019/063108, filed Nov. 25, 2019 and titled "CATHETER AND TUBE ASSEMBLY AND METHOD OF USE," which claims priority benefit of U.S. Provisional Patent Application No. 62/771,154, entitled "Catheter and Tube Assembly and Method of Use," filed Nov. 25, 2018, by Lynn White and U.S. Provisional Patent Application No. 62/771,162, entitled "Catheter and Tube Assembly and Method of Use," filed Nov. 25, 2018, by Lynn White, all of which are incorporated herein by reference.

FIELD

This specification generally relates to draining a fluid from a patient and/or treating the patient.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in-and-of-themselves may also be inventions.

In the prior art, fluids are drained from a patient, via a drainage tube, and medication is delivered to the patient separately.

BRIEF DESCRIPTION OF DRAWINGS

In the following drawings like reference numbers are used to refer to like elements. Although the following figures depict various examples of the invention, the invention is not limited to the examples depicted in the figures.

FIG. 6 shows the location of the detail of FIG. 7.

FIGS. 10B-D show various devices that may be attached to the luer locks of FIGS. 4-10A.

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In general, each of FIGS. 1-12 is discussed in numerical order and the elements within FIGS. 1-12 are also usually discussed in numerical order to facilitate easily locating the discussion of a particular element. Nonetheless, there is no one location where all of the information of any element of FIGS. 1-12 is necessarily located. Unique information about any particular element or any other aspect of any of FIGS. 1-12 may be found in, or implied by, any part of the specification.

Figure 1:
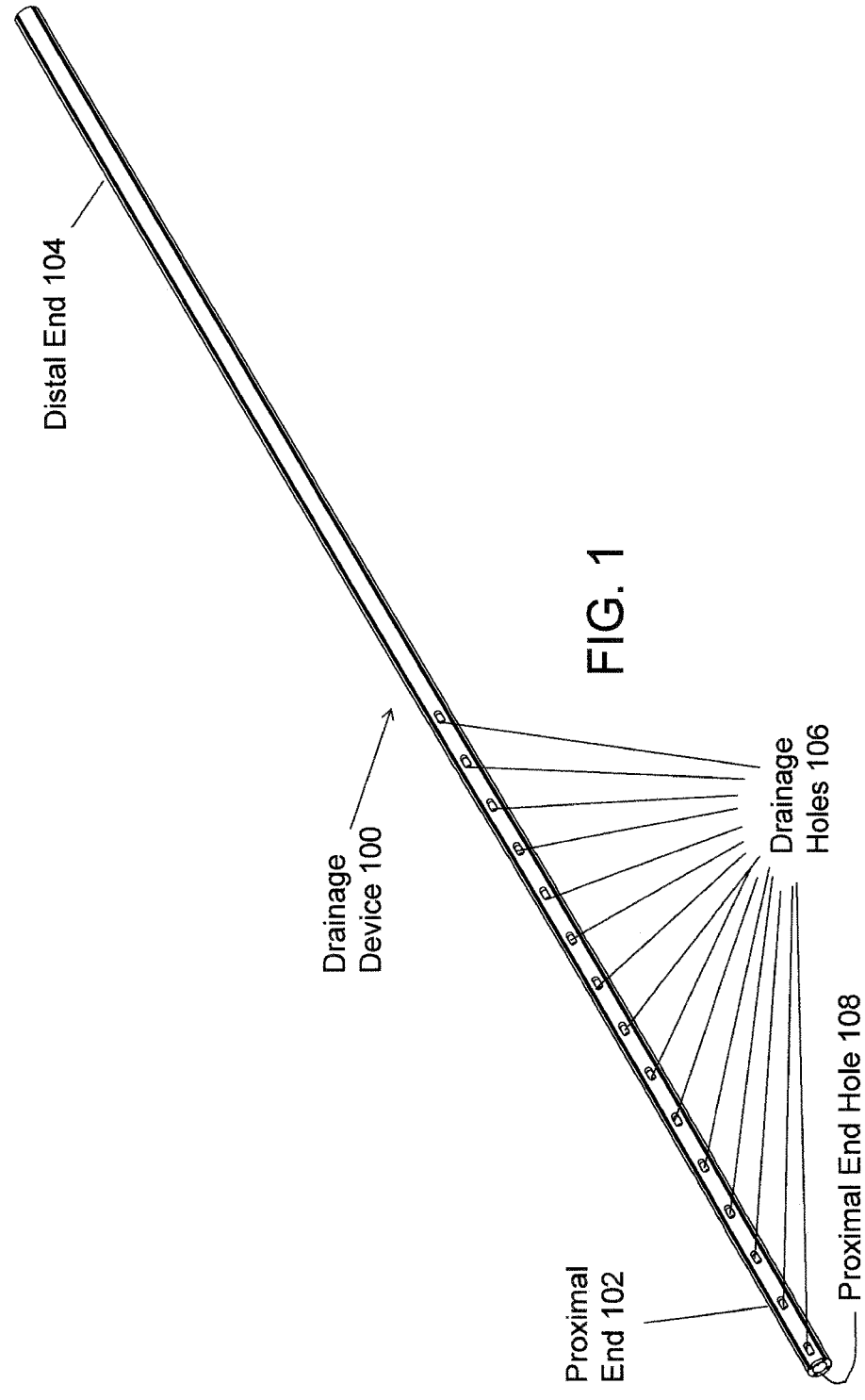
FIG. 1 shows a drawing of a perspective view of an embodiment of a drainage device.

FIG. 1 shows a drawing of an embodiment of a drainage device 100. In an embodiment, drainage conduit 100 may include a distal end 102, proximal end 104, a plurality of drainage holes 106*a-n* (which are referred to collectively as drainage holes 106) along a length of the drainage tube, and end hole 108. In other embodiments drainage device 100 may not have all of the elements or features listed and/or may have other elements or features instead of or in addition to those listed.

Drainage device 100 may include a catheter that delivers medication, such as an analgesic to the patient while draining fluids from a patient. The catheter of drainage device 100 may include a thin tube made from medical grade materials serving a broad range of functions. Drainage device 100 may be a medical device that can be inserted in the body to treat diseases or perform a surgical procedure. Drainage device 100 may be used for cardiovascular, urological, gastrointestinal, and/or neurovascular applications. Drainage device 100 may be used in catheterization and can be inserted into a body cavity, duct, or vessel, to allow drainage, and administration of fluids or gases. Drainage device 100 may be used in Ear, Nose, and Throat (ENT) applications, genitourinary (GU) applications, gynecology (GYN) applications, general surgery, plastic surgery, and/or anywhere body spaces and cavities are entered and a post operation drain and/or infusion is needed, for example.

Drainage device 100 may include a flexible tube assembly (for use as a "soft" catheter). However, different embodiments of drainage device 100 may have varying levels of stiffness depending on the application. Drainage device 100 may be left inside the body, for varying amounts of time depending on the application. In an embodiment, drainage device 100 is open at both ends. Drainage device 100 may be used in a variety of locations within the body of a patient. For example, drainage device 100 may be used in the head, chest, abdomen, genitourinary, extremities, and/or soft tissue areas, among other places.

For example, drainage device 100 may be used as a temporarily thoracic indwelling tube or catheter. Drainage device 100 may be placed in the pleural space in order to drain serous, bloody, malignant, or infected effusions, or to allow air to decompress the space and improve breathing by allowing the lung to expand. The pleural space is bounded by the parietal surface externally, which covers the inner surfaces of the ribs and intercostal spaces and the thoracic surface of the diaphragm, as well as separating the mediastinum form the thoracic cavity. The visceral surface of the pleura is internal and is adherent to the lungs as a membrane. Drainage device 100 may be made of pliable plastic materials or silicone. Perforations may be placed in the distal portion of these conduits in order to drain the pleural space (the term conduit is used to mean a structure that carries a fluid from or to the body). The proximal end is attached to a flexible hose and then to a sealed system on continuous or intermittent suction to evacuate pleural contents.

Placement of drainage device 100 in the body is variable, but in general, when used in the thorax, drainage device 100 may be placed in the pleural space via a surgical incision or through a small incision between two ribs anterolaterally, in the mid axillary line. In sternotomy cases, for open-heart surgeries, a pleural space cannulation may be performed (e.g., with drainage device 100) to avoid accumulation of serosanguinous fluid after surgery from the site of takedown of an internal mammary artery for grafting. Drainage device 100 may be brought out of the body by incisions in the upper abdominal wall. In general, drainage device 100 may be left in the body for a variable amount of time, depending on the clinical situation. In the case of thoracotomy or open heart surgeries, drainage device 100 may be left in place for 3-5 days. In the case of malignant effusions, drainage device 100 may be left in place longer and placed for home use. Optionally, drainage device 100 may be sutured to the skin with a nonabsorbable suture.

Drainage device 100 may help in overcoming/avoiding pleuritic pain that may otherwise occur from having a foreign body in the pleural space (and/or other locations), when using drainage device 100 as the drainage device. Regarding thoracic drainage, without adequate medication or use of drainage device 100, patients may experience referred pain from the movement of the drain against the parietal (external) surface of the pleura, which is innervated by the phrenic and intercostal nerves. The parietal pleura is sensitive to touch, pain, pressure, and temperature. Drainage device 100 may help avoid pain that may otherwise occur at the exit of the drain from the body, between the ribs. Without proper medication or with a prior art drainage system, the pain between the ribs would be due to the stimulation of the parietal pleura having a perforation for the exit of the drainage system, and/or would be due to movement against the drainage system, as the patient moves and breathes.

A benefit of at least one embodiment of drainage device 100, when used as a thoracic catheter is to alleviation pain at the site of the indwelling cannula (where drainage device 100 may be the indwelling cannula), as the indwelling cannula would lie against the parietal pleura on its inner surface. Drainage system 100 may offer a time-released elution of local anesthetic.

Using drainage device 100 it may not be necessary to remove suction in order deliver a local anesthetic and it may not be necessary to keep the suction off to allow the anesthetic dwell long enough for absorption of the dose, since drainage of intrapleural contents (or contents of another area) may occur simultaneously while the administering medication.

Distal end 102 of drainage device is placed outside of the patient's body when deployed and may be attached to a pump or a suction device (e.g., a "grenade"), for example, to create suction that drains fluids from the patient's body.

Proximal end 104 of drainage device is placed in the patient's body when deployed. Proximal end 104 may also be used for delivering intermittent boluses of local anesthetic into the pleural space. Proximal end 104 may also be used for delivering intermittent boluses of local anesthetic into the pleural space or other region. Proximal end 104 of the channel may be the elution portion lying inside the pleural space and eluting local anesthetic into the pleural space.

Drainage holes 106 for draining fluids form a body. In other words, drainage device 100 may include a plurality of drainage holes 106 along the length of the drainage device 100 toward the proximal end of the drainage device 100, and drainage holes 102 lies within the patient's body when drainage device 100 is deployed. In an embodiment, drainage holes 106 have a length of 0.77 cm+/−0.077 cm and a width of 0.38 cm+/−0.038 cm. However, in other embodiments, drainage holes 106 may have other dimensions.

End hole 108 is another drainage hole for draining fluids from the body.

Fluids enter drainage device 100, via drainage holes 106 and/or end hole 108 and exit drainage device 100, via an opening at distal end 102 of drainage device 100.

Figures 2, 3:
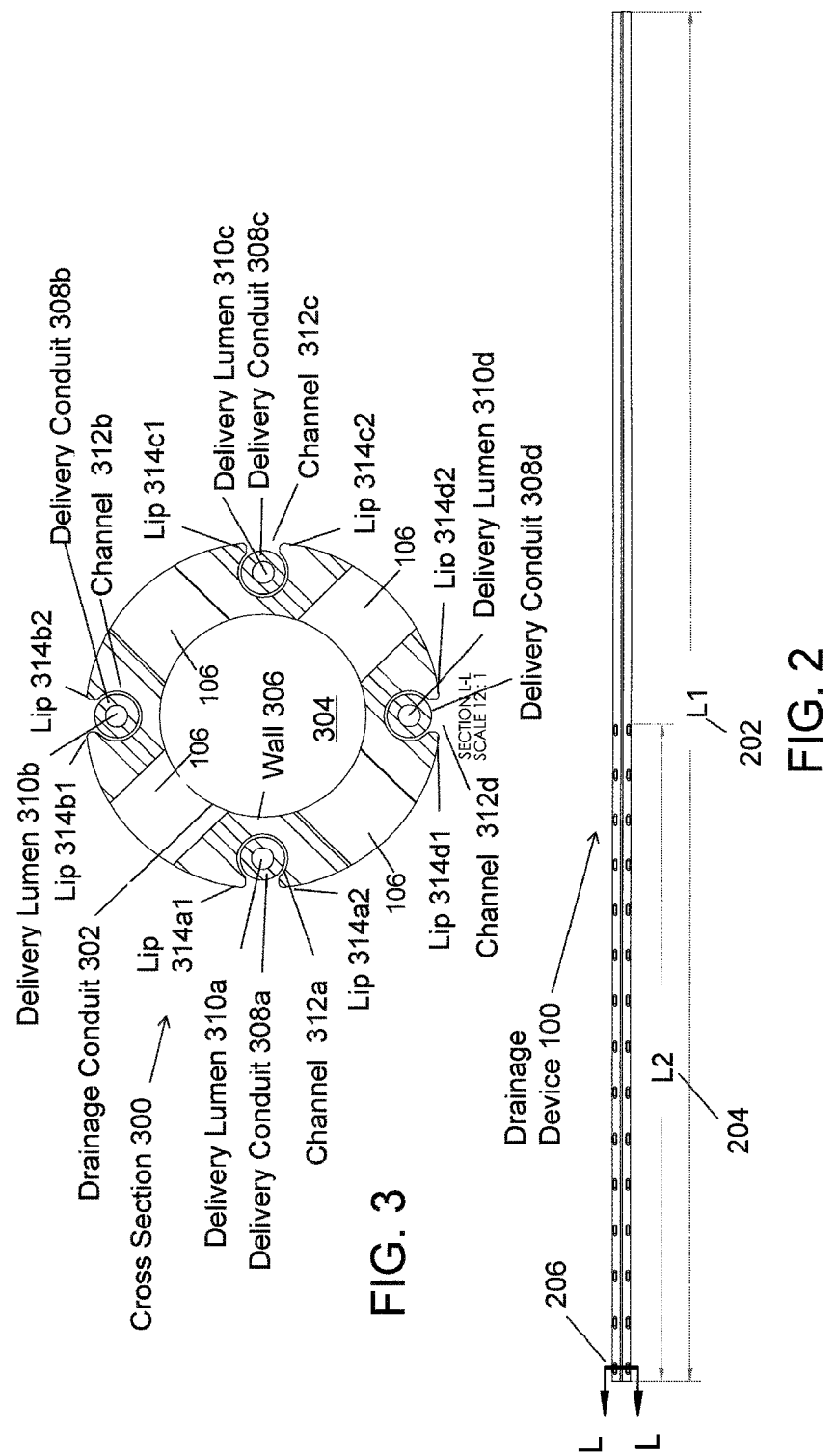
FIG. 2 shows a drawing of a side view of an embodiment of the drainage device of FIG. 1.
FIG. 3 shows a drawing of a cross section of the drainage device FIG. 1 taken along cut L-L of FIG. 2.

FIG. 2 shows a drawing indicating dimension of an embodiment of drainage device 100. In an embodiment, drainage device 100 has a total length L1 202, drainage portion length L2 204, and cut L-L 206.

Total length L1 202 is the total length of the drainage device 100. The lengths shown in the FIG. 2 and discussed below, allow for adjustability of the drainage system, giving surgeons the ability to cut each individual tubing segment to the desired length on a procedure-by-procedure basis. In an embodiment, total length L1 202 may be 70 cm. In an embodiment, total length L1 202 may be 67 cm-73 cm, 65 cm-75 cm, 67 cm-77 cm, or 60 cm-80 cm.

Drainage portion length L2 204 is the portion of drainage device 204 that includes the plurality of drainage holes 106. In an embodiment, drainage portion may be the last 30 cm of the proximal end 104 of drainage device 100. In an embodiment, the drainage portion is 43% of the total length 202. In an embodiment, drainage portion length L2 204 may be 29 cm-31 cm, 28.5 cm-31.5, cm 27 cm-33 cm, or 25 cm-35 cm. In an embodiment, drainage portion length L2 204 may be 41%-44% of, or 40%-45% of, the total length L1 202.

Cut L-L 206 shows the location at which the cross section of FIG. 3 is taken (which is discussed in conjunction with FIG. 3).

FIG. 3 shows a drawing of cross section 300 of drainage device 100 taken along cut L-L of FIG. 2. Cross section 300 includes drainage holes 106, drainage conduit 302, drainage lumens 304, wall 306, delivery conduits 308*a-d* (collectively referred to delivery conduits 308), delivery lumens 310*a-d* (collectively referred to as lumens 310), channels 312*a-d* (collectively referred to as channels 312), and lips 314*a*1-*d*2 (collectively referred to as lips 314). In other embodiments, cross section 300 of drainage device 100 may not have all of the elements or features listed and/or may have other elements or features instead of or in addition to those listed.

The scale of FIG. 3 is 12 time that of FIGS. 1 and 2. Drainage holes 106 are also shown in FIGS. 1 and 2. In other words, drainage holes 106 exist along the proximal length of the tubing (of drainage device 100).

Drainage conduit 302 is the portion of drainage device 100 through which fluids drain from the patient's body. In an embodiment, drainage conduit 302 has an outer diameter of 1.5 cm+/−0.15 cm, and an inner diameter of 0.87 cm+/−0.087 cm. However, in other embodiments, drainage conduit 302 may have other dimensions. Drainage lumen 304 is the lumen (a bore of a tube—as of a hollow catheter) within drainage conduit 302 which carries the fluids out of the body. In an embodiment, drainage lumen 304 is centrally located within drainage conduit 302 and/or drainage device 100. Wall 306 is the wall of drainage conduit 302. In an embodiment, wall 306 forms a cylindrical tube. In other embodiment, drainage conduit 302, drainage lumen 304, and/or wall 306 may have other shapes (e.g., oval-shaped, hexagonal square, rectangular, and/or polygonal). Delivery conduits 308 deliver medication into the body of the patient. In an embodiment, drainage conduit 302 and/or delivery conduit 308 may be made from a flexible material, such as silicone or a plastic. For example, drainage conduit 302 and delivery conduit 308 may be made from polysiloxanes, or other polymers that include a synthetic compound that includes of repeating units of siloxane, (which is a chain of alternating silicon atoms and oxygen atoms, combined with carbon, hydrogen, and occasionally other elements).

Delivery lumens 310 are the lumens within delivery conduits 308 within which medication travels. In an embodiment, delivery conduits 308 are tubular, having a circular inner and a circular outer cross section. In another embodiment inner and/or outer cross sections of delivery conduits 308 have other shapes (e.g., oval-shaped, hexagonal square, square, rectangular, and/or polygonal). Channels 312 are channels within wall 306, which hold delivery conduits 308. In an embodiment, the inner surface of delivery conduits 308 has the same contour as the outer surface of delivery conduits 308. In an embodiment, delivery channels 312 hug delivery conduits 308 holding delivery conduits 308 in place until delivery conduits 308 are peeled out of channels 312 before or after drainage device 100 is deployed in the patient's body. In an embodiment, the radius of the surface of wall 306 is slightly smaller than the radius of the outer surface of delivery conduits 308, so as to create a friction fit. Lips 314 are lips on channels 312, which cover delivery conduits 308, so that an exposed surface of delivery conduits 308 is flush with external surface of wall 306, which is the external surface of drainage conduit 302.

In an embodiment, there are four delivery conduits 308 and four channels 312. In other words, in an embodiment, five independent lumens—one central segment for drainage and four radial segments for elution of analgesics, antibiotics, and/or contact kill, for example. In an embodiment, eluting tubing (delivery conduits 308) is joined to the drainage tubing by peelable sections of material. In an embodiment, tubing (delivery conduits 308) cannot slide back and forth relative to one another. In an embodiment, delivery conduit 308 has an outer diameter of 0.15 cm+/−0.015 cm and an inner diameter of 0.87 cm+/−0.087 cm. However, in other embodiments, delivery conduit 308 may have other dimensions.

In another embodiment, there are a different number of delivery conduits 308 and channels 312 (e.g., 2, 3, 4, 5, 6, 7, or 8 for example). In an embodiment, in a cross section that is perpendicular to the length of drainage device 100 (that is a cross sectional plane having its normal parallel to the axis of the drainage device 100), four drainage holes along the circumference of drainage conduit 302. In an embodiment, there are as many drainage holes 106 as channels 312 in a given perpendicular cross section, such as cross section L-L that has drainage holes 106. In another embodiment, the number of drainage holes 106 in a given cross section having drainage holes, the number of drainage holes is different than the number of channels 312 (where each cross section is taken along a cut that is parallel to cut L-L). In an embodiment, different cross sections of the drainage conduit 302 have drainage holes 106 in different locations. For example, one cross section may only have a top drainage hole 308b, one cross section may only have a bottom drainage hole 308d, one cross section may only have a left drainage hole 308a, one cross section may only have a right drainage hole 308c, one cross section may only have top and bottom drainage holes 308b and d, and/or one cross section may only have a left and a right drainage holes 308a and c, for example.

Figures 4, 5:
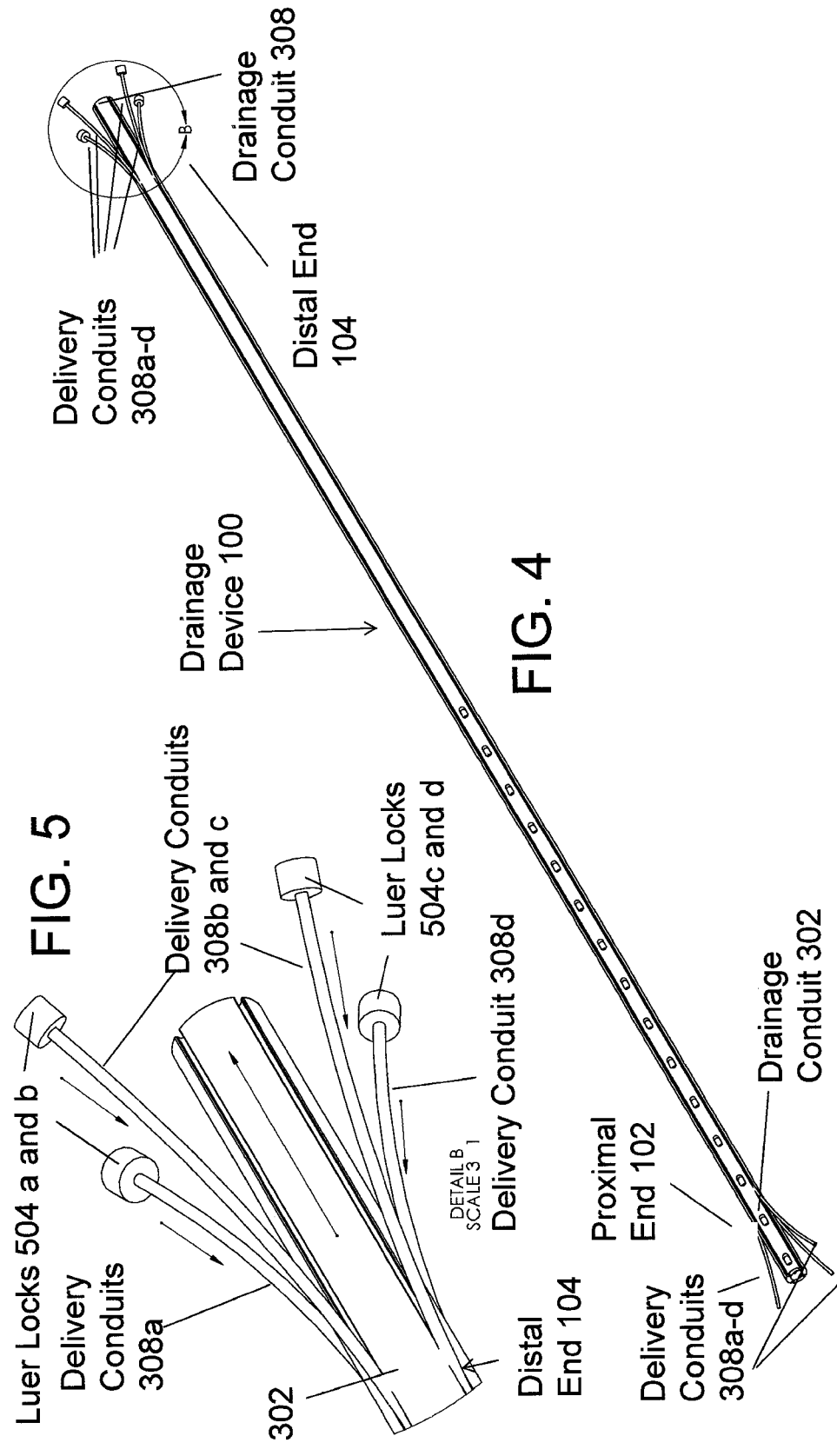
FIG. 4 shows a drawing of an embodiment of drainage device of FIG. 1 in which the delivery conduits have been peeled off the drainage conduit at both the proximal end and distal end.
FIG. 5 shows a drawing of an embodiment of a detail of the distal end of drainage device in which the delivery conduits have been peeled off the drainage conduit.

FIG. 4 shows a drawing of an embodiment of drainage device 100 in which delivery conduits 308 have been peeled off drainage conduit 302 at both the proximal end 102 and distal end 104. FIG. 4 shows the location of Detail B at distal end 104.

FIG. 5 shows a drawing of an embodiment of detail B, detail 500 of device 100 in which delivery conduits 308 have been peeled off drainage conduit 302. Distal ends 104 of delivery conduits 308 may include luer locks 504a-d (referred to collectively as luer locks 504). In other embodiments, detail 500 of drainage device 100 may not have all of the elements or features listed and/or may have other elements or features instead of or in addition to those listed.

The scale of FIG. 5 is 3 time that of FIGS. 1, 2, and 4. Syringes, pumps, and/or reservoirs of medication may be attached to luer locks 504 for adding medication into delivery lumens 310 of delivery conduits 308. Luer lock 504 may include a connector having a luer taper. In an embodiment, leur lock 504 conforms to the ISO 80369, which is incorporated herein by reference. Luer lock 504 may be connected via a tabbed hub on a female fitting that screw into threads in a sleeve on the male fitting. Luer lock 504 may be a "two piece luer lock," or "rotating collar luer lock." Luer lock 504 may be a free rotating collar, or may connect to a free rotating collar, that threads to the luer taper. Luer lock 504 may be locked by rotating the collar. The luer lock 504 has a luer taper that forms a leak-free connections between a male-taper fitting and its mating female part on medical and laboratory instruments, including syringe tips and needles or stopcocks and needles. In other embodiments, another fluid tight connector may be used instead of a luer lock. Luer lock 504 may be either the female collar of the male tape fitting.

Luer locks 504 keep the distal ends of delivery lumens closed and sealed when medication is not being introduced. In FIG. 5 distal ends 502 of delivery conduits 308 have been peeled out of channels 313. Regarding the tubing separation/peel-ability, both the distal and proximal ends of the eluting tubing are capable of being peeled away from the central drainage tubing. Distal ends of the eluting tubing can be peeled to allow for independent and flexible connection to infusion equipment and/or other injection tubes, syringes, for example. Proximal ends of the eluting tubing (delivery lumens 310) can be peeled away to allow for manipulation and situations within the surgical site, as needed by the surgeon. Flow within the drainage tube (drainage conduit 308) and multiple eluting tubes are independent and opposite of each other. The central drainage tube (drainage conduit 302) flows out of the patient. Flow within the drainage tube will be dictated by a vacuum system that is positioned extracorporeally. In an embodiment, there are multiple eluting tubes (delivery conduits 308) via which fluids (e.g., medications) may flow into the patient. The flow within the eluting tubes (drainage conduit 302) can be dictated by a variety of mechanisms (e.g. pain pump, syringe, infusion pump, etc.). The distal ends of the eluting tubing (drainage conduit 308) will be equipped with luer locks for independent connection to injection sources. Within drainage conduit 308, a flow arrow is illustrated showing the direction of the flow of the fluids draining from the body. Adjacent delivery conduits 504 are flow arrows that show the direction of flow of the medication being delivered through the delivery conduits to the body (as indicated by the direction of the flow arrows, the direction of the flow within delivery conduits 504 is the opposite direction as in drainage conduit 308).

Figures 6, 7:
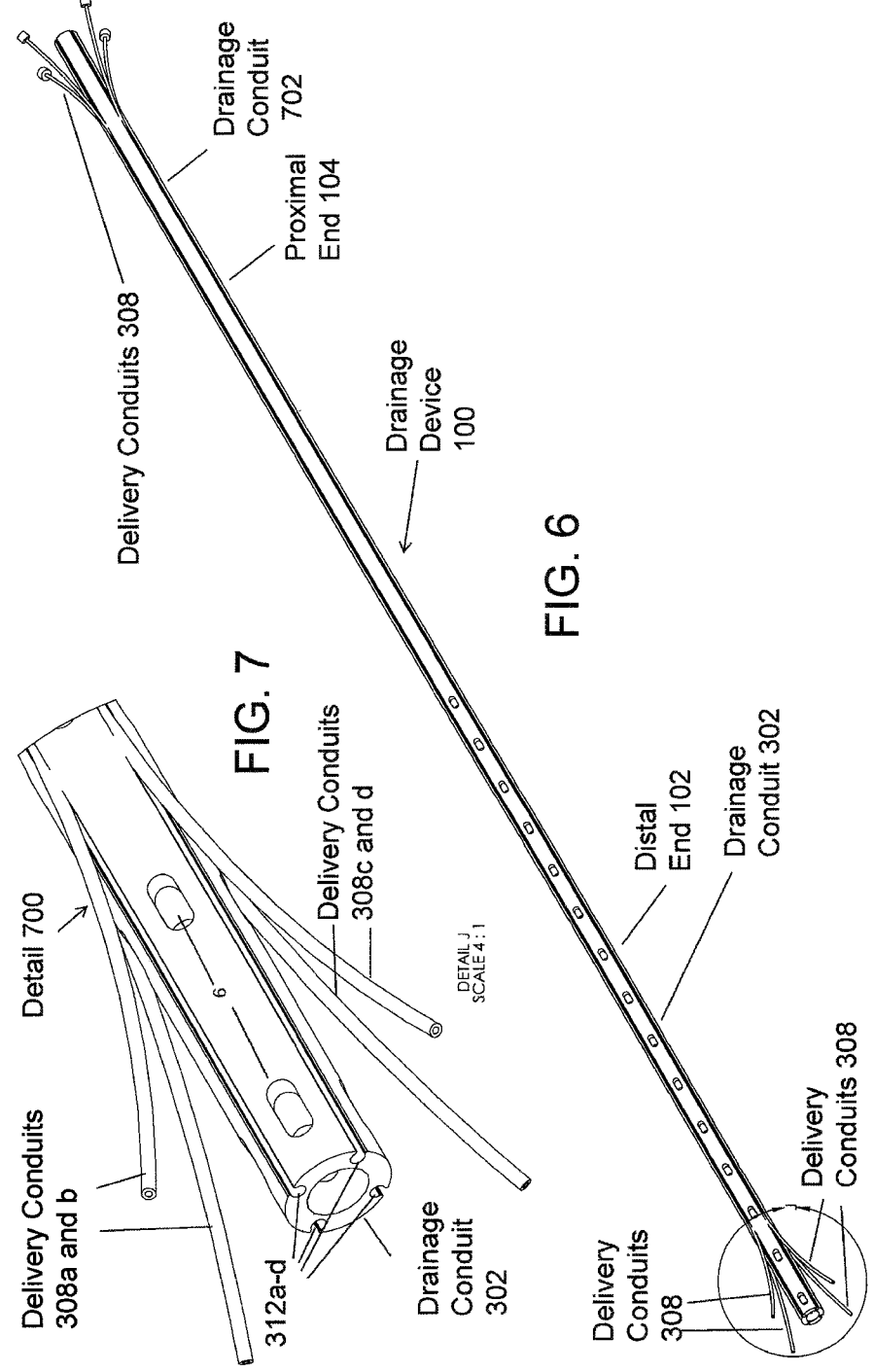
FIG. 6 is essentially the same as FIG. 4. However, in contrast to FIG. 4.
FIG. 7 shows an enlarged view of an embodiment of the detail whose location was indicated in FIG. 6.

FIG. 6 is the same as FIG. 4. However, whereas FIG. 4 shows the location of the detail of FIG. 5, FIG. 6 shows the location of detail J.

FIG. 7 shows a detail 700, which is detail J of the proximal end 102, of the drainage device 100 with the delivery conduits 308.

The scale of FIG. 7 is 4 time that of FIGS. 1, 2, 4, and 6. In FIG. 7, proximal ends 102 of delivery conduits 308 have been peeled out of channels 312. Surgeons have the ability to clip eluting tubes in the desired area for controlled placement of analgesics and other medication. For example, a surgeon may allow placement of eluting tubing (delivery conduits 308) at the patient's skin site for pain relief.

Figures 8, 9:
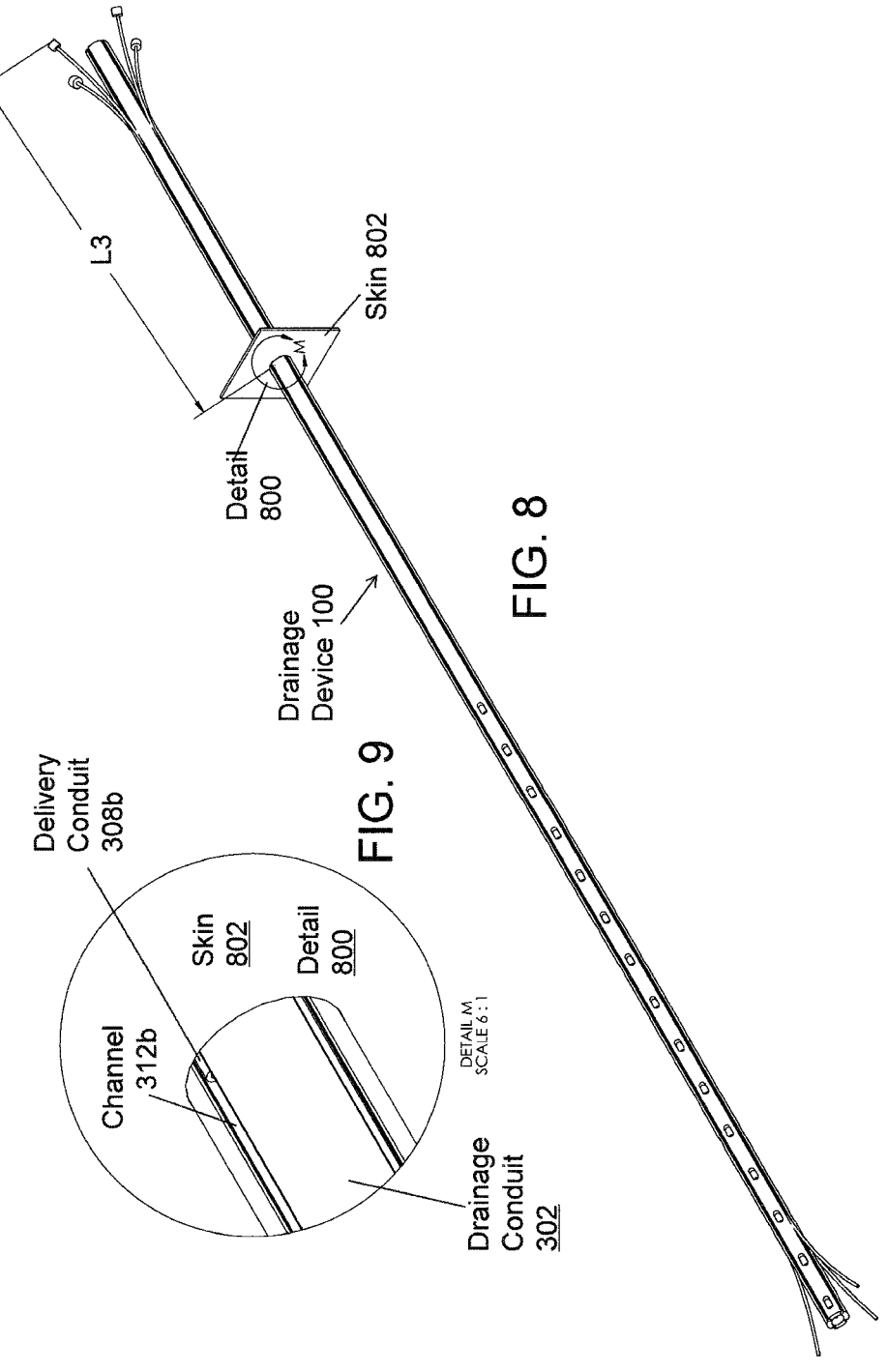
FIG. 8 shows a location of the detail of FIG. 9.
FIG. 9 shows an enlarged view of an embodiment of the detail whose location is indicated in FIG. 8.

FIG. 8 shows detail 800 of drainage device 100 after being deployed. Detail 800 shows the location of skin 802 and detail 804. The location of skin 802 is the location of the skin of the patient when drainage device 100 is deployed, which may a distance L3 from the distal end 102, which is location where it may be desirable to treat with an analgesic and/or other medication. The distance L3 may be determined, by the surgeon, at the time of deployment, based on the patient and/or the location of other equipment.

FIG. 9 shows an embodiment of a detail 802 of drainage device 100. Detail 900 has delivery conduits 308 in channels 312. The scale of FIG. 9 is 6 time that of FIGS. 1, 2, 4, 6, and 8. In FIG. 9, one of delivery conduits 308 has been cut, so that medication is delivered/applied in the vicinity of the skin. One purpose of the system illustrated in FIG. 9 is so that surgeons and other practitioners, may cut the proximal portion of drainage device 100 to adapt drainage device 100 to the patient's size and the configuration needed for that patient. After the drainage device 100 is cut, the drainage device 100 may be connected to an external suctioning device. The drug infusion channel (e.g., one of delivery conduits 308) may thus be spared by peeling one of delivery conduits 308 away from the outer surface of the tube, so that the delivery conduit would not be cut when the chest tube is trimmed. The distal end of this delivery conduit may be connected to a separate adaptor compatible with a luer lock device. Then the luer lock device may connect to a balloon reservoir that holds local anesthetic and a regulator for rate of administration of a medication.

Figure 10A:
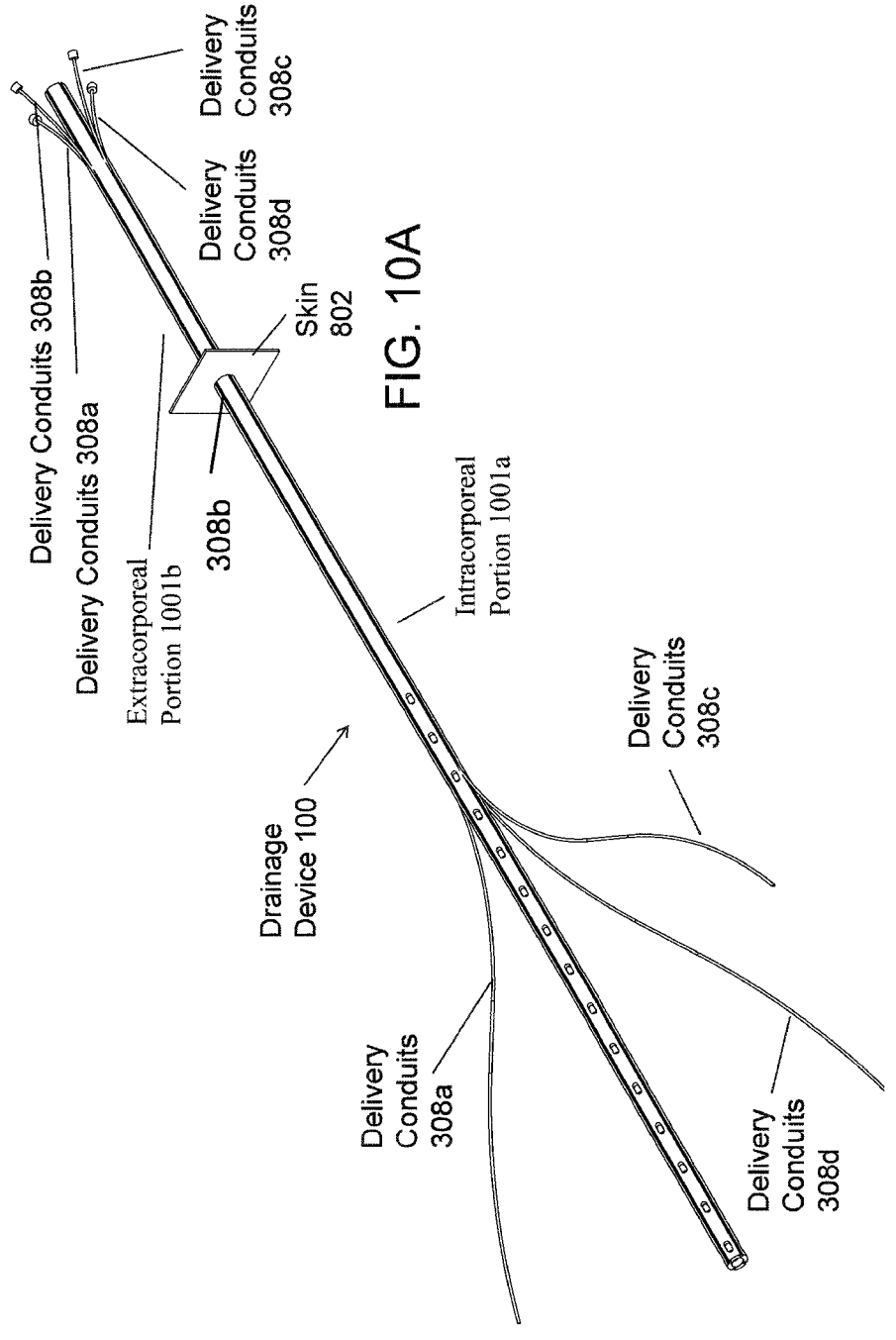
FIG. 10A represents a manner in which the drainage device of FIG. 1 may be deployed.

FIG. 10A represents a manner in which drainage device 100 may be deployed, in situ.

Intracorporeal portion 1001a is the portion of drainage device 100 is that is placed in the body. Extracorporeal portion 1001b is the portion of drainage device 100 is that is placed outside of the body. In FIG. 10A, delivery conduits 308a-d have been peeled at both the proximal end 102 and the distal 104. However, although delivery conduits 308a, c, and d deliver medication into the interior of the body, delivery conduit 308b has been cut in the vicinity where the drainage device 100 is clamped to skin 800, and consequently the proximal end of delivery conduit 308b is not visible in FIG. 10A. The label 308b on the intracorporeal portion 1001a shows the general vicinity where delivery conduit 308b was cut (as indicated in FIG. 9). The eluting tubing, which is delivery conduits 308a, c, and d, may peel away from drainage tubing for intracorporeal placement desired by surgeon drainage device 100 may be secured in place, via extracorporeal sutures.

FIGS. 10B-C show various devices that may be attached to luer locks 504. FIG. 10B shows a representation of a syringe 1002, which may be attached to one of delivery conduits 308a-d, via one of luer locks 504a-d. The user may squeeze the syringe to cause mediation to be delivered to the patient, via one of delivery conduits 308a-d.

FIG. 10C shows a representation of a reservoir 1004, which may be attached to one of delivery conduits 308a-d, via one of luer locks 504a-d. Reservoir 1004 may be a bag storing medication. By keeping reservoir 1004 suspended above the proximal end of delivery conduits 308a-d, gravity will cause mediation in reservoir 1004 to flow, via one of delivery conduits 308a-d to the patient.

FIG. 10D shows a representation of a pump 1006 connected to a reservoir 1008 and one of luer locks 504a-d. Pump 1006 pumps medication in reservoir 1008 through one of delivery conduits 308a-d to the patient.

Figure 10E:
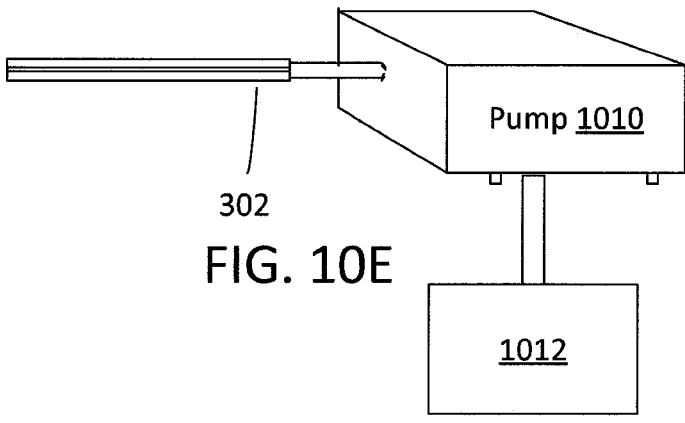
FIGS. 10E and 10F show various devices that may be attached to the drainage conduit.
Figure 10F:
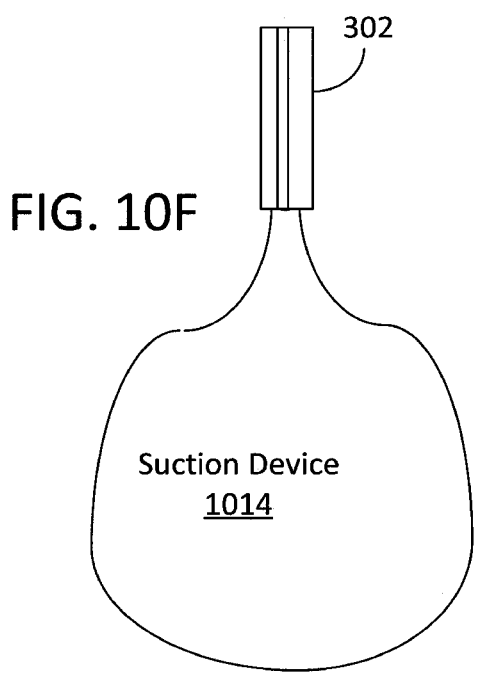

FIGS. 10E and 10F show different devices that may be attached to drainage device 100 to assist in draining fluid from the patient.

FIG. 10E shows a representation of a pump 1010 connected to a container 1012 and drainage conduit 302. Pump 1010 pumps fluids from the patient, via drainage conduit 302 to container 1012. Once container 1012 is full container 1012 and/or its contents may be discarded.

FIG. 10F shows a representation of suction device 1014. One may squeeze suction device 1014 to at least partially remove air from suction device 1014, and then without allowing suction device 1014 to completely refill with air, suction device 1014 may be attached to drainage conduit 308, so as to create suction that draws fluids out of the patient.

Although FIGS. 10E and 10F show pump 1010 and suction device 1014 connected directly to drainage conduit 302, there may be a connector and/or other components between drainage conduit 302 and pump 1010 and/or suction device 1014. Optionally, drainage conduit may have a collar portion without any channel at distal 104, to which other devices may attach. Optionally drainage conduit 302 may have threading on the inner wall 306, so that drainage conduit may be sewed to another device.

Method of Use

Figure 11:
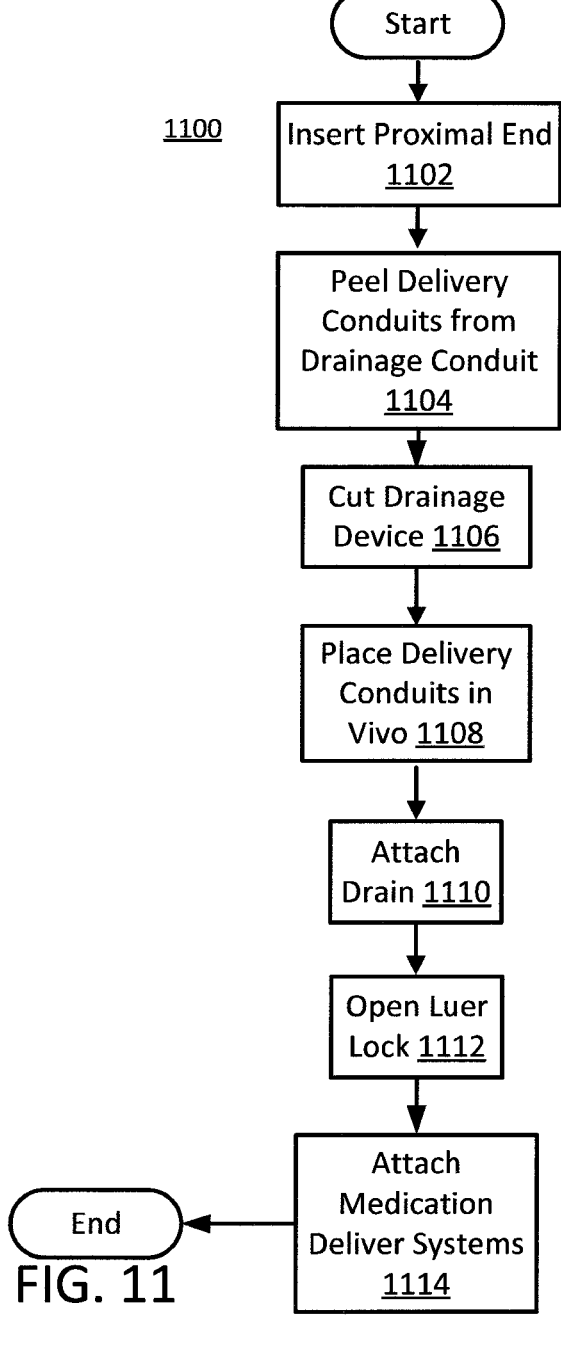
FIG. 11 shows a flowchart of an embodiment of a method of using drainage device.

FIG. 11 shows a flowchart 1100 of an embodiment of method of using drainage system 100.

In step 1102, the proximal end of the drainage conduit 302 and/or drainage device 100 is inserted into the patient with the portion of the delivery conduit 308 that lie in channels 312 (prior to peeling the delivery conduits 308 out the channels 312).

In step 1104, a portion of a flexible delivery conduit is peeled from a flexible drainage conduit 302 at a proximal end and/or distal end of the flexible drainage conduit 302, while leaving a region the flexible delivery conduits 308 at least partially attached to the flexible drainage conduit 302. The flexible delivery conduit is peeled from the drainage conduit 302 at the distal end of the flexible delivery conduits 308 prior to delivering the medication via the flexible delivery conduits 308. The peeling may also include removing the flexible delivery conduit from a channel in an exterior of the flexible drainage conduit.

In step 1106, drainage device 100 is cut to a desired length. Optionally, one of delivery conduits 308 may be cut in at a location that is near skin of the patient, so as to deliver medication to a region in a vicinity of the skin.

In step 1108, the delivery conduits 308*a, b, c,* and/or d are peeled from the drainage conduit 302 at the proximal end, intracorporeally, and placed in vivo at locations determined based on the needs of medication for different regions of the body of the patient. Medication is subsequently delivered (optionally delivery conduits 308 may be peeled at the proximal end (intracorporealy) at an earlier time after the step 1102).

In step 1110, the drain (e.g., a suction device) is attached to the drainage conduit 302 and fluids from the patient are drained via the flexible drainage conduit 302.

In step 1112, a luer lock is opened on the distal end of the flexible delivery conduit after peeling the delivery conduit from the drainage conduit, so as to deliver medication.

In step 1114, medication is delivered to the patient via the flexible delivery conduit 302.

In an embodiment, each of the steps of method 1100 is a distinct step. In another embodiment, although depicted as distinct steps in FIG. 11, step 1104-1114 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

Method of Making

Figure 12:
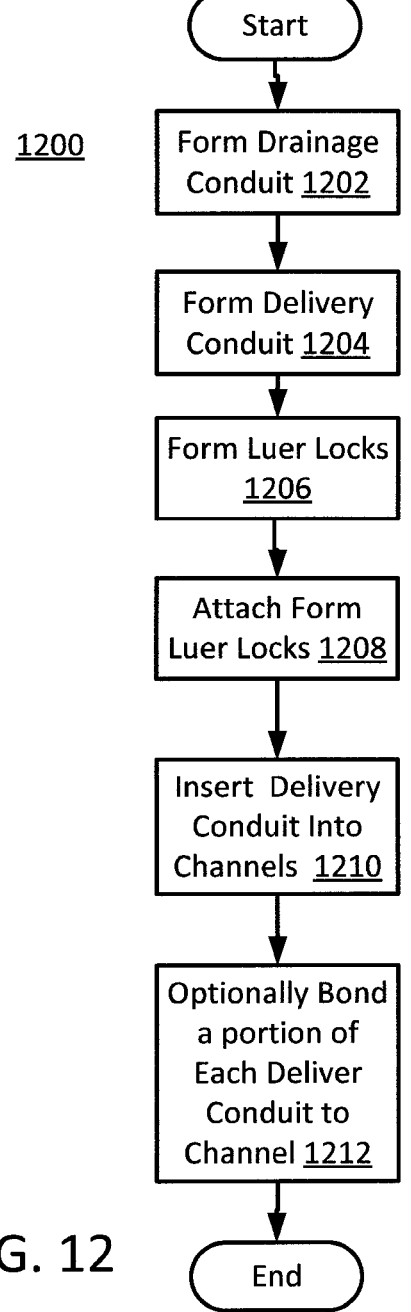
FIG. 12 shows a flowchart of an embodiment of a method of making drainage device.

FIG. 12 shows a method 1200 of making drainage device 1200. In step 1202, drainage conduit 308 is formed. Drainage conduits 308 may be formed with drainage holes 106 and/or channels 310 and/or may first be formed with channels 310 (e.g., by molding drainage device 100). Alternatively, drainage conduit 302 may be formed without drainage holes 106 and with or without channels 310 (e.g., by extrusion), and then drainage holes 106 may be cut into wall 306 of drainage conduit 308. As another embodiment, drainage conduit 302 is first formed without either drainage holes 106 or channels 106, which are both later formed in wall 306. The drainage holes 106 are formed at a proximal end of drainage conduit 308 and/or drainage device 100.

In step 1204, delivery conduits 308 are formed. In step 1206 luer locks are formed. In step 1208, luer locks are attached to the distal end of delivery conduits 308.

In step 1210, delivery conduits 308 are inserted into channels 310, such that the distal and proximal ends of delivery conduits 308 may be peeled away from drainage conduit 302. In an embodiment, delivery conduits 308 are held in place lips 312 and/or by a friction fit—that is, by the friction caused by the walls of channel 310 hugging the exterior surface of delivery conduit 308. In an embodiment, the friction the friction caused by the walls of channel 310 hugging the exterior surface of delivery conduit 308 also prevents delivery conduits 308 from sliding within channels 310. In optional step 1212, a portion of delivery conduits 308 are permanently bonded into channels 310 (while leaving the distal and proximal ends of delivery conduits peelable from drainage conduit 308 and/or channels 310). For example, the bonding may be performed by heating at least the channels 310 in the region where it is desired to bond the channels 310 to delivery conduits 308 thereby melting the exterior surface of delivery conduits 308 and/or wall 306, which upon cooling forms a bond. Alternatively, a bonding material may inserted between the exterior walls of delivery conduit 308 and wall 306 to form a bond. The bonding material may be an adhesive or a material that melts at a lower temperature than the material from which delivery conduit 308 and wall 306 are made. Alternatively or additionally, the bonded portion may be wrapped (e.g., shrink wrapped) with a wrapping to help hold delivery conduits 308 attached to drainage conduit 302.

In an embodiment, each of the steps of method 1200 is a distinct step. In another embodiment, although depicted as distinct steps in FIG. 12, step 1202-1212 may not be distinct steps. In other embodiments, method 1200 may not have all of the above steps and/or may have other steps in addition to or instead of those listed above. The steps of method 1200 may be performed in another order. Subsets of the steps listed above as part of method 1200 may be used to form their own method.

EXAMPLES OF EMBODIMENTS

Embodiment 1. A device comprising:

a flexible drainage conduit 302 for draining fluids from a patient; and a one or more flexible delivery conduits 308 for delivering medication to the patient, the one or more flexible delivery conduits 308 being attached to the flexible drainage conduit 302, the one or more flexible delivery conduits 308 being detachable from the flexible drainage conduit 302 at at-least one end of the drainage conduit 302.

Embodiment 2. The device of any of embodiments 1-35 or 1, the one or more flexible delivery conduits 308 being detachable at both a proximal end of the flexible delivery conduit and a distal end of the flexible drainage conduit 302.

Embodiment 3. The device of any of embodiments 1-35 or 1, the one or more flexible delivery conduits 308 being permanently connected to the drainage conduit 302 at a location between a first end of the drainage conduit 302 and a second end of the drainage conduit 302.

Embodiment 4. The device of any of embodiments 1-35 or 1, wherein the one or more flexible delivery conduits 308 include at least two flexible delivery conduits 308.

Embodiment 5. The device of any of embodiments 1-35 or 1, wherein the one or more flexible delivery conduits 308 include at least two flexible delivery conduits 308 located at an exterior surface of the drainage conduit 302 equally spaced concentrically around the flexible delivery conduits 308.

Embodiment 6. The device of any of embodiments 1-35 or 1, wherein the one or more flexible delivery conduits 308 include four flexible delivery conduits 308.

Embodiment 7. The device of any of embodiments 1-35 or 1, the flexible drainage conduit 302 having one or more channels 312 that hold the one or more delivery conduits 308.

Embodiment 8. The device of any of embodiments 1-35 or 7, the one or more channels 312 each surrounding one of the one or more the delivery conduits 308 on at least 180 degrees of a circumference of the delivery conduit.

Embodiment 9. The device of any of embodiments 1-35 or 7, the channel surrounding the delivery conduit such that an exposed surface of the delivery conduit is flush with an outer surface of the drainage conduit 302.

Embodiment 10. The device of any of embodiments 1-35 or 1, the drainage conduit 302 having a plurality of drainage holes along a length of the drainage conduit 302 being closer to a first end of the flexible drainage conduit 302 that is proximal than a second end that is distal end of the drainage conduit 302 that is distal.

Embodiment 11. The device of any of embodiments 1-35 or 1, the one or more flexible delivery conduits 308 having one or more lure locks 504 at a distal end of the one or more flexible delivery conduits 308.

Embodiment 12. The device of any of embodiments 1-35 or 1, wherein the delivery conduit is flexible.

Embodiment 13. A device comprising:

a flexible drainage conduit 302 for draining fluids from a patient; and the flexible drainage conduit 302 having a plurality of channels 312 located on an exterior surface of the flexible drainage conduit 302;

a plurality of flexible delivery conduits 308 for delivering medication to the patient, the plurality of flexible delivery conduits 308 being located in the plurality of channels 312, such that exposed surfaces of the plurality of flexible delivery conduits 308 are flush with an exterior of the drainage conduit 302;

the plurality of flexible delivery conduits 308 being permanently attached to the flexible drainage conduit 302 at a location between a first end of the conduit that is at a distal end and a second end of the drainage conduit 302 that is at the proximal end of the drainage conduit 302, the plurality to flexible delivery conduits 308 being detachable attached to the flexible drainage conduit 302 at the first and the second end; and the flexible drainage conduit 302 having a plurality of drainage holes along a length of the drainage conduit 302 closer to the second end than the first end.

Embodiment 14. A method comprising:

peeling a portion of a flexible delivery conduit from a flexible drainage conduit 302 at a proximal end of the flexible drainage conduit 302, while leaving a region the flexible delivery conduit at least partially attached to the flexible drainage conduit 302;

inserting the proximal end of the drainage conduit 302 into the patient with the portion of the delivery conduit that was peeled from the drainage conduit 302;

draining fluids from the patient via the flexible drainage conduit 302; and delivering medication to the patient via the flexible delivery conduits 308.

Embodiment 15. The method of any of embodiments 1-35 or 14, further comprising:

peeling the flexible delivery conduit from the drainage conduit 302 at the distal end of the flexible delivery conduit prior to delivering the medication, via the flexible delivery conduits 308.

Embodiment 16. The method of any of embodiments 1-35 or 14, further comprising:

opening a luer lock on the distal end of the flexible delivery conduit after peeling the delivery conduit from the drainage conduit 302, so as to deliver medication.

Embodiment 17. The method of any of embodiments 1-35 or 14, further comprising:

puncturing a hole in the flexible delivery conduit at a location that is near skin of the patient, so as to deliver medication to a region in a vicinity of the skin.

Embodiment 18. The method of any of embodiments 1-35 or 14, the peeling further comprising removing the flexible delivery conduit from a channel in an exterior of the flexible drainage conduit 302.

Embodiment 19. The method of any of embodiments 1-35 or 18, an exposed surface of the flexible delivery conduit being flush with an exterior surface of the drainage conduit 302.

Embodiment 20. The method of any of embodiments 1-35 or 14, the flexible delivery conduit being one of a plurality of flexible delivery conduits 308.

Embodiment 21. The method of any of embodiments 1-35 or 14, wherein the delivery conduit is flexible.

Embodiment 22. A method comprising:

forming a drainage conduit for draining fluids from a patient; and forming a one or more flexible delivery conduits for delivering medication to the patient, the one or more flexible delivery conduits being attached to the drainage conduit, the one or more flexible delivery conduits being detachable from the drainage conduits at at-least one end of the drainage conduit.

Embodiment 23. The method of any of embodiments 1-35 or 22, the one or more flexible delivery conduits being detachable at both a proximal end of the flexible delivery conduit and a distal end of the drainage conduit.

Embodiment 24. The method of any of embodiments 1-35 or 22, further comprising permanently connecting the one or more flexible delivery conduits to the drainage conduit at a location between a first end of the drainage conduit and a second end of the drainage conduit.

Embodiment 25. The method of any of embodiments 1-35 or 22, wherein the one or more flexible delivery conduits include at least two flexible delivery conduits.

Embodiment 26. The method of any of embodiments 1-35 or 22, wherein the one or more flexible delivery conduits include at least two flexible delivery conduits located at an exterior surface of the drainage conduit equally spaced concentrically around the flexible delivery conduit.

Embodiment 27. The method of any of embodiments 1-35 or 22, wherein the one or more flexible delivery conduits include four flexible delivery conduits.

Embodiment 28. The method of any of embodiments 1-35 or 22, further comprising forming one or more channels in the drainage conduit for holding the one or more delivery conduits.

Embodiment 29. The method of any of embodiments 1-35 or 28, the one or more channels each being formed to surround one of the one or more the delivery conduits on at least 180 degrees of a circumference of the delivery conduit.

Embodiment 30. The method of any of embodiments 1-35 or 28, the channel surrounding the delivery conduit being formed such that an exposed surface of the delivery conduit is flush with an outer surface of the drainage conduit.

Embodiment 31. The method of any of embodiments 1-35 or 22, forming a plurality of drainage holes in the drainage conduit along a length of the drainage conduit being closer to a first end of the drainage conduit that is proximal than a second end that is distal end of the drainage conduit that is distal.

Embodiment 32. The method of any of embodiments 1-35 or 22, attaching one or more luer locks to a distal end of the one or more flexible delivery conduits.

Embodiment 33. The method of any of embodiments 1-35 or 22, wherein the drainage conduit is flexible.

Embodiment 34. The method of any of embodiments 1-35 or 22, the forming the drainage conduit including extruding the drainage conduit.

Embodiment 35. The method of any of embodiments 1-35 or 22, the forming the one or more delivery conduits including extruding the one or more delivery conduits.

Alternatives and Extensions

Drainage device 100 may deliver anesthetics such as lidocaine, bupivacaine or other long-acting liposomal bupivacaine, such as Exparel® (or other medications). Exparel® can produce the desired effects of local anesthetic for a period of 48 to 72 hours in a single administration Another long acting anesthetic currently in use for post-operation pain management, and. Exparel® does not interfere with polypropylene or silicone, and as with other local anesthetics, is not known to be irritating to tissues. Other non-opioid or opioid analgesics may be also be used.

In an alternative embodiment, the center lumen is used for delivery of medication, and the other lumens are used for drainage of the patient. In an embodiment, a drainage tube may have a membrane, which may have a gel consistency, and/or may be a gel matric. The membrane may elute medication (the medication may be extracted as a result of the membrane dissolving) with the activated surface in contact with tissues optionally in a time-release manner. The concentrations of local anesthetics may be an amount that is not to be irritating or toxic to tissues. Additionally or alternatively, drainage device 100 may have a wrapper to keep the distal portion protected from dehydration, as the membrane would be activated upon contact with the pleural surface.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A device comprising:

a drainage conduit for draining fluids from a patient; and one or more flexible delivery conduits for delivering medication to the patient, the one or more flexible delivery conduits being attached to the drainage conduit, the one or more flexible delivery conduits being held in respective channels on an exterior surface of the drainage conduit such that an exposed surface of each of the one or more flexible delivery conduits is substantially flush with an outer surface of the drainage conduit, wherein the one or more flexible delivery conduits are detachable from the drainage conduit at a proximal end and a distal end of the drainage conduit by peeling the delivery conduits from the channels.

2. The device of claim 1, wherein the one or more flexible delivery conduits are permanently connected to the drainage conduit at a location between a first end of the drainage conduit and a second end of the drainage conduit.

3. The device of claim 1, wherein the one or more flexible delivery conduits include at least two flexible delivery conduits.

4. The device of claim 1, wherein the one or more flexible delivery conduits include at least two flexible delivery conduits located at an exterior surface of the drainage conduit and disposed in channels equally spaced concentrically around the drainage conduit.

5. The device of claim 1, wherein the one or more flexible delivery conduits include four flexible delivery conduits.

6. The device of claim 1, the drainage conduit having one or more integral channels that hold the one or more flexible delivery conduits.

7. The device of claim 6, the one or more channels each surrounding a respective delivery conduit of the one or more flexible delivery conduits on at least 180 degrees of a circumference of the respective delivery conduit.

8. The device of claim 6, each channel surrounding a respective one of the one or more flexible delivery conduits such that an exposed surface of the respective one of the one or more flexible delivery conduits is substantially flush with an outer surface of the drainage conduit.

9. The device of claim 1, the drainage conduit having a plurality of drainage holes along a length of the drainage conduit being closer to a proximal end of the drainage conduit than a distal end of the drainage conduit.

10. The device of claim 1, the one or more flexible delivery conduits having one or more Luer locks at a distal end of the one or more flexible delivery conduits.

11. The device of claim 1, wherein the drainage conduit is flexible.

* * * * *